(12) United States Patent
Shtakelberg et al.

(10) Patent No.: US 7,225,682 B2
(45) Date of Patent: Jun. 5, 2007

(54) METHOD, APPARATUS AND SYSTEM FOR MONITORING HARDENING AND FORECASTING STRENGTH OF CEMENTITIOUS MATERIAL

(75) Inventors: David Shtakelberg, Jerusalem (IL); Shimon Boiko, Har Adar (IL); Boris Wilge, Doar Na Merkaz (IL); Oscar Milman, Maale-Adumim (IL)

(73) Assignee: Concretec Ltd., Jerusalem (IL)

( * ) Notice: Subject to any disclaimer, the term of this patent is extended or adjusted under 35 U.S.C. 154(b) by 0 days.

(21) Appl. No.: 10/872,393

(22) Filed: Jun. 22, 2004

(65) Prior Publication Data

US 2005/0279178 A1    Dec. 22, 2005

(51) Int. Cl.
*G01N 3/00*    (2006.01)
(52) U.S. Cl. .................................................... 73/803
(58) Field of Classification Search ............... 324/300, 324/690; 73/73, 803
See application file for complete search history.

(56) References Cited

U.S. PATENT DOCUMENTS

| | | | |
|---|---|---|---|
| 2,654,862 A | 6/1953 | Petersen | |
| 2,656,508 A | 10/1953 | Coulter | |
| 3,278,844 A | 10/1966 | Bell et al. | |
| 4,524,319 A | 6/1985 | Eberling et al. | |
| 5,672,968 A * | 9/1997 | Miller et al. | 324/300 |
| 6,396,265 B1 * | 5/2002 | Shtakelberg et al. | 324/300 |
| 6,756,793 B2 * | 6/2004 | Hirono et al. | 324/690 |
| 2003/0079995 A1 | 5/2003 | Contolini et al. | |
| 2004/0099532 A1 | 5/2004 | Hachman, Jr. et al. | |

FOREIGN PATENT DOCUMENTS

| | | |
|---|---|---|
| CA | 2322931 | 4/2002 |
| EP | 0243681 | 4/1987 |
| JP | 02-284051 | 11/1990 |
| RU | 483623 | 5/1975 |
| RU | 1176227 | 8/1985 |
| RU | 2127366 | 3/1999 |

OTHER PUBLICATIONS

Brameshuber et al. "Electrical Conductivity Measurement to Characterize the Setting and Hardening of Mortars", Trans. Internat. Symposium of Non-Destructive Testing in Civil Engineering, Deutsche Gesellschaft f. Zerstörungsfreie Prüfung e.V., p.1-9, 2003.
Backe et al. "Characterizing Curing Cement Slurries by Electrical Conductivity", SPE Drilling & Completion, 16(4): 201-207, 2001. p. 204-205, Figs.2, 3, 10.

* cited by examiner

*Primary Examiner*—Jewel V. Thompson

(57) ABSTRACT

A method of monitoring a strengthening process of a chemically active material having a liquid phase and a non-liquid phase, the method comprises: (a) continuously measuring at least one physical parameter characterizing the liquid phase; (b) extracting a time-dependence of the at least one physical parameter, so as to identify functional transitions in the time-dependence; and (c) using the functional transitions to determine a strengthening state of the chemically active material; thereby monitoring the strengthening process of the chemically active material.

59 Claims, 11 Drawing Sheets

METHOD, APPARATUS AND SYSTEM FOR MONITORING HARDENING AND FORECASTING STRENGTH OF CEMENTITIOUS MATERIAL

FIELD AND BACKGROUND OF THE INVENTION

The present invention relates to a method, apparatus and system for monitoring hardening forecasting strength of chemically active materials, and, more particularly, to a method, apparatus and system for non-destructive forecasting of concrete strength, at an early hardening stage.

As used herein throughout the specification and in the claims section below, the phrase "chemically active material(s)" includes cementitious materials, such as, but not limited to, cement paste, mortar, concrete, lime, gypsum, clay and the like that undergo a curing process when hardening.

A chemically active material often needs to be analyzed so as to determine the structural properties parameters, particularly strength and other physical-mechanical properties of the final cured product, such as its potential for shrinkage. The final strength of a chemically active capillary-porous material is determined by the properties of the initial raw materials, mixing and compacting conditions, and specific composition such as, but not limited to, mineral binder-to-aggregate ratio, water-to-cement ratio, water-to-aggregate ratio and the like [Neville A. M., "Properties of concrete," Longman Scientific & Technical, 1981].

Traditional prior art methods for testing the strength of concrete typically require 28 days to complete. The builder usually does not or cannot delay construction 28 days to receive the test results. Rather, the construction usually continues in the hope that the concrete is sound. If in the final analysis, the concrete does not meet the standards, the building may have to be reinforced or even torn down, perhaps incurring major additional costs.

Improvements in cement production and prediction of concrete performance properties require the application of material science. Methods of predicting the final strength of concrete while hardening have been developed over the years, based on theoretical and experimental investigations of the crystallization strengthening laws and the properties of chemically active material [to this end see, e.g., Abrams D. A. "Design of concrete mixtures," Bull. No. 1, Sruct. Mater. Lab., Lewis Inst., Chicago, 1918; Powers T. C., "Structure and physical properties of hardened Portland cement paste," J. Amer. Ceramic. Soc., 41, 1958, pp. 1–6; Roy D. M. and Gouda G. R., "Porosity-strength relation in cementitious materials with very high strength," J. Amer. Ceramic. Soc., 53, No. 10, 1973, pp. 549–550; Sheikin A. E., Chekhovsky I. V. and Brusser M. I., "Structure and properties of cementitious concrete," Stroyizdat Press, Moscow, 1973 (in Russian)].

In modern plants, the preparation of a chemically active material is typically fully automated and computer-controlled. High quality and reliability of the technological equipment and control systems is crucial for providing high quality and stable final product. With respect to concrete, for example, it is desired to optimize the process such that the strength of the concrete, 28-days from preparation is maximal.

One method to predict the concrete strength [King J. W. H., "Further notes on the accelerated test for concrete," Chartered Civil Engineer, London, May 1957, pp. 15–19] includes warming a 6-hour age concrete to 200° F. (93° C.) and extrapolation of the obtained results 7 days and 28 days.

Also known [Y. Ono, "Microscopic observation of clinker for estimation of burning condition, grindability and hydraulic activity," Proc. $3^d$ Intern. Conf. Cem. Microscopy, Houston, 1981; Sinha S. K., Rao L. H. and Akhouri P. H., "Rapid estimation of the 28-day compressive strength of clinker by optical microscopy," Proc. $13^{th}$ Intern. Conf. Cem. Microscopy. ICMA, Florida, April 1991] are attempts to predict the 28-day strength of cement proceeding from the measurement results of Portland cement clinker crystals by means of an electronic microscope.

The above and other prior art methods are expensive and complicated, and require a well equipped laboratory and a highly trained material scientist or technician.

The hardening process of a chemically active material can be considered as a series of consecutive transitions between different states of the material.

Initially, the material is a compaction structure whose physical and mechanical properties are determined mainly by compressive actions of capillary pressure on "water-air" boundaries. This state is characterized by an intensive development of the chemical reactions, such as hydration and hydrolysis and formation of gel (the term gel has been introduced into the scientific practice in conjunction to cementitious materials by T. Powers in an article entitled "The non-evaporable water content of hardened Portland cement pastes," published in ASTM Bulletin, 1949, No. 158, and was further used by A. Neville in an article entitled "Properties of concrete," published by Longman Scientific & Technical, 1961).

In a second state following the initial state, the material develops a coagulation structure, which is a capillary-porous colloidal body having chemically active water-silicate dispersions.

In a third state the material develops a colloidal-crystalline structure, which is a quasi-solid capillary porous body. In this state the gel begins to age and crystalline structures are formed.

In a fourth state, the crystalline structures condensate, and the material has a solid capillary-porous body whose conditions are determined by the laws governing the interaction of particles and particle aggregates in the solid phase.

At any given state, the chemically active material has a poly-dispersed structure of a moist capillary-porous body. The liquid phase of the material is therefore an informative component indicative of the porosity of the material and therefore of its strength. Water (both in a liquid and gaseous form) is always in a state of thermodynamic equilibrium with the porous solid phase with which it interacts. Thus, the properties of water are changing in strict accordance with structure formation and consequently with the strength growth of the hardening material. To this end, see, for example, Shtakelberg D. I. and Sithcov M. M., "Self-organization in disperse systems," Riga, "Zinatne" Press, 1990; and Shtakelberg D. I., "Thermodynamics of water-silicate disperse materials structure-formation," Riga, Zinatne, 1984; and Neville M. "Properties of concrete," Longman Scientific & Technical. NT., 1988.

The duration of the above hardening process is typically rather long. For example, in cementitious materials typical duration of hardening is of order of one month, at which time the cement passes through all the above states and becomes a solid structure of a given compressive strength.

Due to the long duration of the hardening process, prior to reaching the final strength, the chemically active material undergoes many complicated physical and chemical processes, which can essentially affect its physical properties. It is recognized that any change, deviation and non-observance of the technological regulations during preparation of the chemically active material, such as ready-mixed or pre-cast concrete, may irreversibly reduce the properties (e.g., strength) of the final product. Reasons for poor final product quality include unexpected replacement of material suppliers, improper operation of the equipment or failure thereof and the like.

Hardening and strengthening of chemically active material is initiated immediately once the compaction for a particular application is completed. However, many additional processes, affecting the final quality can takes place. For example, in case of concrete, the transportation of the mix from the manufacturing plant to the building site typically occurs between the preparation of the mix and the compaction thereof. Although during transportation the concrete mix is in a continuous motion inside a rotating drum so as to prevent setting or hardening, it is known that the final properties of cementitious products made after a prolonged transportation of the mix are different from the properties of the same products when made of a freshly prepared mix.

Prolonged transportation of the mix naturally extends the period in which chemical reactions such as hydration and hydrolysis occur. Thus, upon arrival to the construction site different transport durations result in different initial states for the hardening and strengthening processes evolve.

Other factors which are known to alter the hardening process include, chemical additives of various functional purposes, temperature conditions during hardening, curing conditions of the freshly formed concrete, non-homogeneity of the mix, complexity and duration of the manufacturing process and the like.

It is therefore recognized that an optimal final product requires a continuous and operative monitoring during manufacturing and throughout the hardening and strengthening stages.

Although the nature of hardening and strengthening processes is, in principle, deterministic, prior art methods and apparati fail to provide an accurate and reliable technique for forecasting strength the strength of the final product by monitoring the hardening and strengthening stages of the mix.

There is thus a widely recognized need for, and it would be highly advantageous to have a method, apparatus and system for monitoring hardening and forecasting strength of cementitious material, devoid of the above limitations.

SUMMARY OF THE INVENTION

According to one aspect of the present invention there is provided a method of monitoring a strengthening process of a chemically active material having a liquid phase and a non-liquid phase, the method comprising: (a) continuously measuring at least one physical parameter characterizing the liquid phase; (b) extracting a time-dependence of the at least one physical parameter, so as to identify functional transitions in the time-dependence; and (c) using the functional transitions to determine a strengthening state of the chemically active material; thereby monitoring the strengthening process of the chemically active material.

According to another aspect of the present invention there is provided a method of determining a strengthening state of a chemically active material from a series of measurements of at least one physical parameter characterizing a liquid phase of the chemically active material, the method comprising extracting a time-dependence of the at least one physical parameter, so as to identify functional transitions in the time-dependence, and using the functional transitions to determine the strengthening state of the chemically active material.

According to further features in preferred embodiments of the invention described below, the step of continuous measurement is executed substantially in a constant volume.

According to still further features in the described preferred embodiments the step of continuous measurement is initiated sufficiently before a compressive strength of the chemically active material develops a logarithmic time-dependence.

According to still further features in the described preferred embodiments the step of continuous measurement is initiated when an age of the chemically active material is below about 150 hours, more preferably below about 100 hours, most preferably below about 50 hours.

According to still further features in the described preferred embodiments the at least one physical parameter is selected from the group consisting of electrical resistivity and electrical resistance.

According to still further features in the described preferred embodiments the method further comprises correlating between the time-dependence of the at least one physical parameter and the compressive strength, thereby obtaining a correlation function.

According to still further features in the described preferred embodiments the method further comprises using the correlation function for parameterizing the logarithmic time-dependence of the compressive strength curve.

According to still further features in the described preferred embodiments the step of continuous measurement comprises positioning the chemically active material in a container and generating an electric field within the chemically active material, so as to measure the resistivity or resistance of the chemically active material.

According to still further features in the described preferred embodiments the generation of the electric field is by at least two electrodes and further wherein the continuous measurement comprises measuring at least one component of electrical current flowing through the at least two electrodes.

According to still further features in the described preferred embodiments the at least one component of electrical current is a real-part of the electrical current.

According to still further features in the described preferred embodiments the at least one component of electrical current is an imaginary-part of the electrical current.

According to still further features in the described preferred embodiments the method further comprises contouring the electric field substantially along a predetermined contour within the chemically active material.

According to still further features in the described preferred embodiments the contouring the electric field is by positioning a dielectric partition in a manner such that electric field lines of the electric field bypass the dielectric partition hence being contoured along the predetermined contour.

According to still further features in the described preferred embodiments the contouring the electric field is by generating an additional electric field in a manner such that an effective electric field, defined by a superposition of the electric field and the additional electric field, is contoured along the predetermined contour.

According to yet another aspect of the present invention there is provided an apparatus for determining a strengthening state of a chemically active material from a series of measurements of at least one physical parameter characterizing a liquid phase of the chemically active material, the apparatus comprising: (a) an inputting unit for inputting the series of measurements; (b) an extractor for extracting a time-dependence of the at least one physical parameter; and (c) an identifier for identifying functional transitions in the time-dependence, and using the functional transitions for determining the strengthening state of the chemically active material.

According to further features in preferred embodiments of the invention described below, the apparatus further comprises a correlator for correlating between the time-dependence of the at least one physical parameter and a compressive strength of the chemically active material, thereby obtaining a correlation function.

According to still further features in the described preferred embodiments the apparatus further comprises a parameterizer for parameterizing a curve of the compressive strength, using the correlation function, wherein the curve has a logarithmic shape.

According to still another aspect of the present invention there is provided an apparatus for measuring an electrical resistance of a chemically active material, the apparatus comprising: (a) a container for holding the chemically active material; (b) at least two electrodes for generating an electric field within the chemically active material and sensing a resistance of the chemically active material to the electric field; and (c) a contouring device for contouring the electric field substantially along a predetermined contour within the chemically active material.

According to an additional aspect of the present invention there is provided a system for monitoring a strengthening process of a chemically active material having a liquid phase and a non-liquid phase, the system comprising: (a) a measuring apparatus for continuously measuring at least one physical parameter characterizing the liquid phase; and (b) an analyzing apparatus, for determining a strengthening state of the chemically active material thereby monitoring the strengthening process, the analyzing apparatus comprises an extractor, for extracting a time-dependence of the at least one physical parameter, and an identifier, for identifying functional transitions in the time-dependence and using the functional transitions for determining the strengthening state.

According to further features in preferred embodiments of the invention described below, the measuring apparatus comprises: (i) a container for holding the chemically active material; (ii) at least two electrodes for generating an electric field within the chemically active material and sensing a resistance of the chemically active material to the electric field; and (iii) a contouring device for contouring the electric field substantially along a predetermined contour within the chemically active material.

According to still further features in the described preferred embodiments the contouring device comprises a passive contouring device.

According to still further features in the described preferred embodiments the passive contouring device comprises a dielectric partition, positioned between a first electrode and a second electrode of the least two electrodes, and further wherein a size and shape of the dielectric partition is selected such that electric field lines of the electric field bypass the dielectric partition hence being contoured along the predetermined contour.

According to still further features in the described preferred embodiments the contouring device comprises an active contouring device.

According to still further features in the described preferred embodiments the active contouring device comprises an arrangement of additional electrodes designed and configured such that an effective electric field, defined by a superposition of an electric field generated by the additional electrodes and the electric field generated by the at least two electrodes, is contoured along the predetermined contour.

According to still further features in the described preferred embodiments the arrangement of additional electrodes comprises at least one linear electrode.

According to still further features in the described preferred embodiments the arrangement of additional electrodes comprises at least one electrode having a circular-like shape.

According to still further features in the described preferred embodiments the arrangement of additional electrodes comprises a first electrode, a second electrode and a third electrode, and further wherein a potential difference across the first electrode is selected such that a potential difference between the second electrode and the third electrode is substantially zero at all times.

According to still further features in the described preferred embodiments the arrangement of additional electrodes comprises a first pair of electrodes, a second pair of electrodes and a third pair of electrodes, wherein a potential difference across the first pair of electrodes is selected such that a potential difference between the second pair of electrodes and the third pair of electrodes is substantially zero at all times.

According to still further features in the described preferred embodiments the functional transitions are characterized by a sign inversion of an nth derivative of the time-dependence, the n being a positive integer.

According to still further features in the described preferred embodiments the functional transitions comprise deviations of the time-dependence from smoothness.

According to still further features in the described preferred embodiments the functional transitions comprise at least one inflection point of the time-dependence.

The present invention successfully addresses the shortcomings of the presently known configurations by providing a method, apparatus and system for monitoring hardening and forecasting strength of cementitious material, far exceeding prior art teachings.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
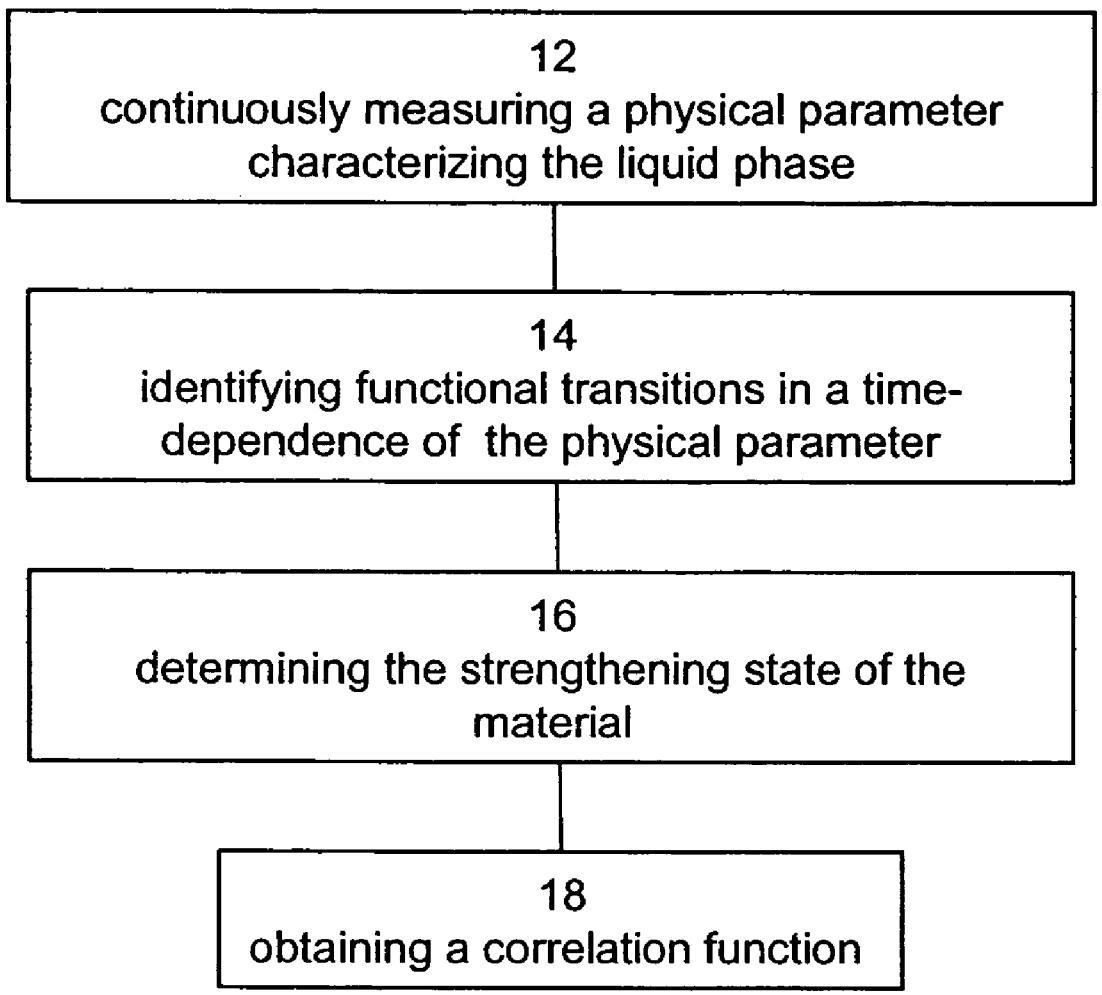
FIG. 1 is a flowchart diagram of a method of monitoring a strengthening process of a chemically active material, according to a preferred embodiment of the present invention.

The present invention is of a method, apparatus and system for monitoring strengthening of chemically active materials, which can be used for forecasting strength of various compositions and structures. Specifically, the present invention can be used to forecast strength of a structure made of a cementations material, such as, but not limited to, concrete.

The principles and operation of a method, apparatus and system for monitoring strengthening of chemically active materials according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Hardening and strengthening of chemically-active materials ensue from a joint development of complex physical and chemical processes. The motivating force of these processes is the chemical reaction of hydration as well as the hydrolyzation of the mineral binders (cement, gypsum, lime, etc.) present in the material. As soon as a sufficient amount of product resulting from these reactions is accumulated per volume unit, a capillary-porous structure begins to form, first as a coagulation structure (long-range and short-range), and thereafter as colloidal and crystallization structures.

While at the beginning of the development of the hydration and hydrolysis the properties acquired by the material are reversible, once short-range coagulation structure is formed, the properties of the material become irreversible.

The reason of the reversibility at the beginning of the development of the hydration and hydrolysis is the long-range coagulation structure of the material. This structure features thixotropic properties which allow for reverse processes, e.g., under application of certain mechanical action, to occur. On the other hand, in the short-range coagulation structure, the formation of the initial crystalline frame finalizes all mechanical transitions within the material hence preventing reverse processes from occurring.

Thus, the crystallization strengthening process deterministically evolves from the initial conditions set at the time of short-range coagulation structure formation. As these initial conditions depend on the mechanical state of the material when its structure still has a long-range nature, it is appreciated that mechanical transitions occurring at that time substantially determine the subsequent crystallization of the material, hence also its strength.

The present inventors have devised a method, apparatus and system which are capable of monitoring the strengthening process of chemically active materials, preferably at early hardening stages. The present invention can be used by manufacturers of chemically active materials for optimizing their products, for example, by monitoring of the strengthening process and adjusting the various manufacturing steps in real-time, while the properties of the final products are still adjustable.

Thus, according to one aspect of the present invention there is provided a method of monitoring a strengthening process of a chemically active material. The embodiments and examples of the present invention are described herein mostly with reference to the curing of concrete. It is to be understood that the present invention is applicable to any chemically active material having a liquid phase and a non-liquid phase, not exclusively concrete.

Referring now to the drawings, the method comprises the following method steps which are illustrated in the flowchart of FIG. 1. In a first step of the method, designated in FIG. 1 by Block 12, at least one physical parameter characterizing the liquid phase is continuously measured. The physical parameter is preferably an electrical parameter, such as, but not limited to, electrical resistance or electrical resistivity. In this embodiment, the measurement of step 12 is preferably performed by electrical means. Methods and apparati for electrical measurements of chemically active materials are known in the art and can be found, for example, in Achverdow I., "Basis of physics of concrete," Stroyizdat Press, Moscow, 1981; McCarter W., Forde M. and Whittington H., "Resistivity characteristics of concrete," Proc. ICE, Pt. 2, No. 71, 1981, pp. 107–118; Van Beek A., Van Breugel K. and Hilhorst M., "Monitoring system for hardening concrete based on dielectric properties," Dundee: Creating with concrete. Utilizing of ready-mixed concrete and mortar, 1999, pp. 303–312.

According to a preferred embodiment of the present invention the measurement of the physical parameter is preferably substantially in a constant volume. The advantage of this embodiment is that a constant volume of the chemically active material during the measurement ensures that any functional dependence of the measured parameter can be attributed to the strengthening of the material, rather than to its volume. An apparatus suitable for measuring electrical resistance of the chemically active material is further detailed hereinafter.

In a second step of the method, designated in FIG. 1 by Block 14, a time-dependence of the physical parameter is extracted and functional transitions of the time-dependence are identified.

As used herein "functional transition" refers to any detectable mathematical transition of a function, including without limitation, a transition of a given function (e.g., a change of a slope, a transition from increment to decrement or vice versa) and a transition from one characteristic functional behavior to another (e.g., a transition from a linear to a nonlinear behavior or a transition from a first nonlinear behavior to a second, different, nonlinear behavior).

The functional transitions can be identified, for example, by calculating a derivative of the time-dependence and finding zeros thereof. As will be appreciated by one of ordinary skill in the art, whenever a transition of a function is characterized by a zero of one of its derivatives. For example, a transition from increment to decrement or vice versa is characterized by a zero of a first derivative, a transition from a concave region to a convex region or vice versa (points of inflection) is characterized by a zero of a second derivative, etc. According to a preferred embodiment of the present invention any derivative of the time-dependence can be used. Generally, the functional transitions are preferably characterized by a sign inversion of an nth derivative of time-dependence, where n is a positive integer.

Additionally or alternatively the functional transitions can be identified by observing deviations of the time-dependence from smoothness. In this embodiment, the functional transitions can be identified either with or without calculating the derivatives of the time-dependence. For example, deviations from smoothness can be identified manually or by comparing the time-dependence to a known smooth function.

A particular feature of the present invention is the ability to monitor the strengthening process of the chemically active material during the stage in which the properties of the material can still be adjusted, according to the needs of the specific application for which the chemically active material is manufactured. Once the chemically active material passes the reversible stage it enters the irreversible stages of hardening, in which the manufacturer's control on the quality of the final product is very limited. In is known that during the irreversible hardening stages, the compressive strength, R, as a function of time, $\tau$, has a logarithmic shape:

$$R(\tau) = R_n \frac{\log \tau}{\log n}, \qquad \text{(EQ. 1)}$$

where $R_n$ denotes the compressive strength of the material at time $\tau = n$.

According to a preferred embodiment of the present invention, step 12 of the method is initiated sufficiently before the compressive strength of the chemically active material develops a logarithmic time-dependence. For concrete, for example, a preferred age of the mix at which step 12 is initiated is below about 150 hours, more preferably below about 100 hours, most preferably below about 50 hours.

As used herein the term "about" refers to ±10%.

One ordinarily skilled in the art would appreciated that monitoring the strengthening process of concrete at such an early stage is extremely advantageous, because in this stage the concrete manufacturer is provided with a sufficient time to adjust the preparation process according to its needs before the mix enters the aforementioned irreversible hardening stages.

According to a preferred embodiment of the present invention the method further comprises an optional step, designated in FIG. 1 by Block 18, in which the time-dependence of the physical parameter is correlated with the compressive strength so as to obtaining a correlation function. The correlation function can be realized in more than one way. Thus, in one embodiment, the correlation function can preferably has an analytical form, in another embodiment the correlation function preferably has a numerical form (e.g., a table) and in an additional embodiment the correlation function preferably has a graphical form (a calibration curve).

The correlation function can be used for parameterizing the logarithmic time-dependence of $R(\tau)$, characterizing the development of the compressive strength at the later hardening stages. More specifically, denoting the time-dependence of the physical parameter by $\rho(\tau)$ and the correlation function by $\psi$, the value of $R(\tau)$ can be calculated using the following equation:

$$R(\tau) = \psi[\rho(\tau)], \qquad \text{(EQ. 2)}$$

form which the parameterization of Equation 1 can be obtained by selecting an appropriate initial time, n, and calculating $R_n \equiv R(\tau=n)$. In other words, once $\psi$ is known, the compressive strength of the chemically active material, substantially at all times in which the material has a liquid phase, can be calculated using the following equation:

$$R(\tau) = \begin{cases} \psi[\rho(\tau)] & \tau \leq n \\ R_n \dfrac{\log \tau}{\log n} & \tau > n. \end{cases} \quad (\text{EQ. 3})$$

Thus, the present embodiment of the invention successfully provides a method of monitoring the compressive strength, R, of the chemically active material from an early hardening stage, which, in combination with the logarithmic time-dependence characterizing the late hardening stages, can be used to forecast the strength of the final product.

The ability of the present embodiment to monitor the strengthening process accounts for the identification of the functional transitions of the extracted time-dependence of the measured physical parameter. The present inventors have uncovered that these transitions are representative of physical transitions between different states of the chemically active material.

The relation between the functional transitions of the physical parameter and the physical transitions between states can be explained as follows.

While hardening, the chemically active material generally experiences transitions between three states: (i) continues liquid phase and discrete solid phase; (ii) discrete liquid phase and discrete solid phase; and (iii) discrete liquid phase and continues solid phase.

The hydration and hydrolysis developed during the initial state result in accumulation of colloid dispersed crystalline hydrates (particles smaller than 100 Å) and formation of a gel in the system. In this state, the liquid phase is continuous while the solid phase is discrete. The functional transitions in this case are preferably decrement of the electrical resistance or resistivity, caused, inter alia, by the hydration of free lime and increment of alkalinity.

Once the material transforms into its second hardening state, particles of the hydrated phase having very large specific surface begin to interact, to form continuously growing crystalline nuclei. This results in a formation of crystalline aggregates and chains and initiates the discretization of the liquid phase. Note that in this state the solid phase is still discrete. The functional transitions in this case are preferably increment of the electrical resistance or resistivity, caused, inter alia, by the accumulation of the crystalline component.

In the third state of the chemically active material, intensive interactions of solid-phase elements result in a formation of three-dimensional cells of irregular shape and arbitrary volume. The formation of the three-dimensional cells occurs prior to the build-up of a continuous crystalline frame. The functional transitions in this case are preferably stabilization of the electrical resistance or resistivity.

The three-dimensional cells are subjected to a continuous convergence process in which point-like contacts between adjacent cells gradually developed into crystalline interaction surfaces, resulting in a formation of a continuous solid phase having a crystalline form. This process occurs both globally, via the aforementioned interactions between adjacent cells, and locally, via similar interactions within the cells. It has been found by the inventors of the preset invention that the growth of the compressive strength of the chemically active material is related to the convergence process of the three dimensional cells formed during the third state. The transition into a continuous solid phase results in a further discretization of the liquid phase which can be observed, for example, as a sharp increment of the electrical resistance.

Thus, the above three states of the chemically active material can be characterized by the following functional transitions of the electrical resistivity (i) from a decrement to a relatively steep increment; (ii) from the relatively steep increment to a relatively moderate increment; and (iii) from a relatively moderate increment to a sharp increment.

Once the convergence process is completed, the chemically active material behaves as a typical condensation structure with a logarithmic compressive strength time-dependence, as further detailed hereinabove.

According to another aspect of the present invention there is provided an apparatus 20 for measuring electrical resistance of a chemically active material. Apparatus 20 can be used, for example, for implementing the measurement step of the method (see Block 12), in the embodiment in which the physical parameter is electrical resistance or resistivity.

Figure 2:
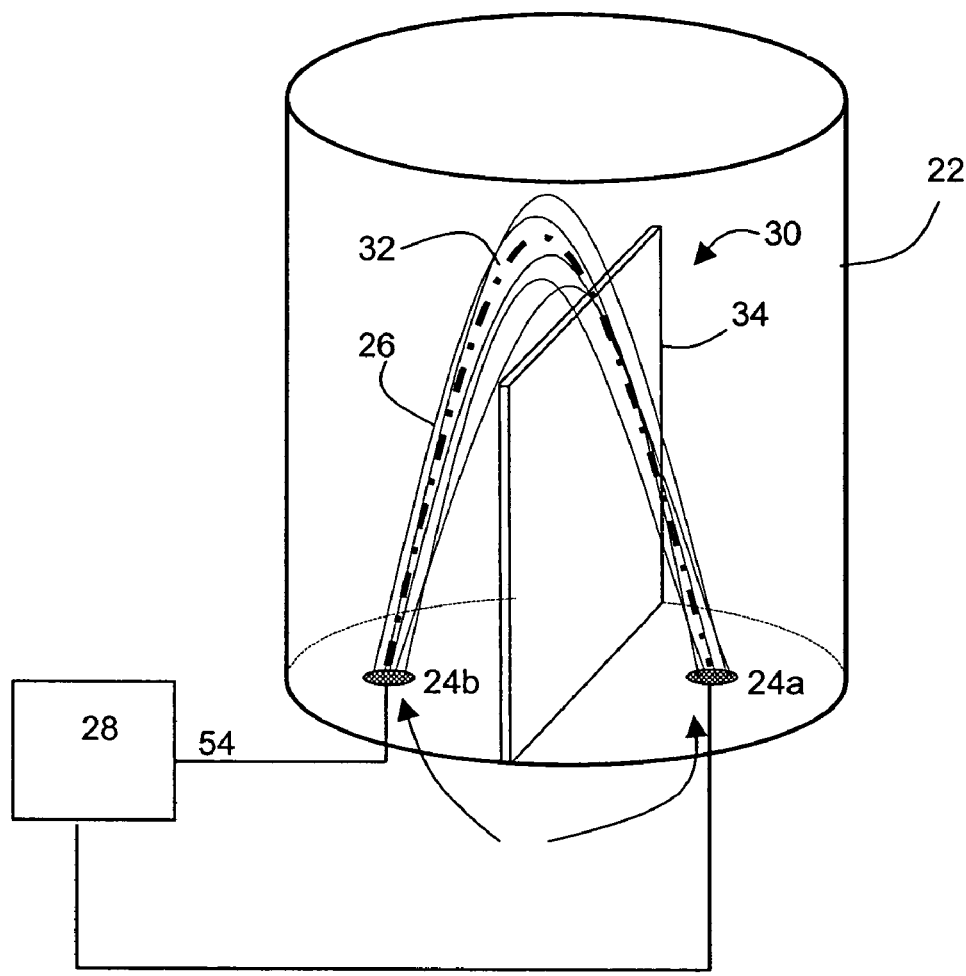
FIG. 2 is a schematic illustration of an apparatus for measuring electrical resistance of a chemically active material, according to a preferred embodiment of the present invention.

Reference is now made to FIG. 2 which is a schematic illustration of apparatus 20, according to a preferred embodiment of the present invention. Apparatus 20 comprises a container 22 for holding the chemically active material and at least two electrodes 24. Electrodes 24 serve for generating an electric field 26 within the chemically active material, and sensing the resistance of the chemically active material to electric field 26. The generation of electric field 26 can be done by connecting electrodes 24 to a voltage source 28, via lead 54. The resistance of the chemically active material can be sensed by measuring a particular component (real-part or imaginary part) of electrical current flowing through electrodes 24.

According to a preferred embodiment of the present invention apparatus 20 further comprises a contouring device 30 for contouring electric field 26 substantially along a predetermined contour 32 within the chemically active material. The contouring of electric field 26 along contour 32 ensures that the density of current which is provided by electrodes 24 is substantially constant at all times, hence facilitating a highly reliable measurement.

The contouring of electric field 26 can be achieved in more than one way.

Hence, in one embodiment, contouring device 30 is a passive contouring device. For example, as shown in FIG. 2, contouring device 30 can comprise a dielectric partition 34, positioned between a first electrode 24a and a second electrode 24b. According to the presently preferred embodiment of the invention a size and shape of partition 34 is selected such that the electric field lines bypass partition 34 hence being contoured along contour 32. A preferred shape of partition 34 is a plane having a diameter similar to the diameter of container 22 and a height which is about 75% of the height of container 22. For example, when container 22 is a cylinder, about 10 cm in diameter and about 16 cm in height, partition 34 is a plane having dimensions of about 10 cm wide and about 8 cm height. It is to be understood that these values are not to be considered as limiting.

Figure 3:
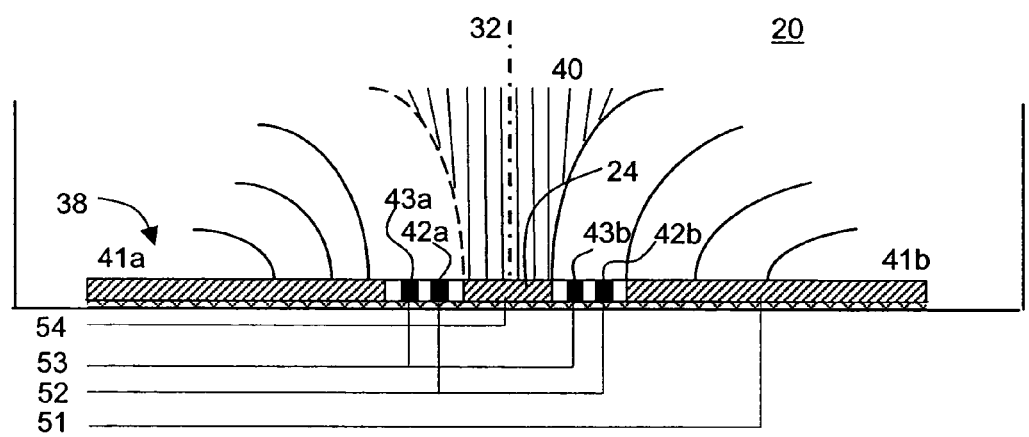
FIG. 3 is a schematic illustration of the apparatus for measuring electrical resistance having an active contouring device, according to a preferred embodiment of the present invention.
Figure 4:
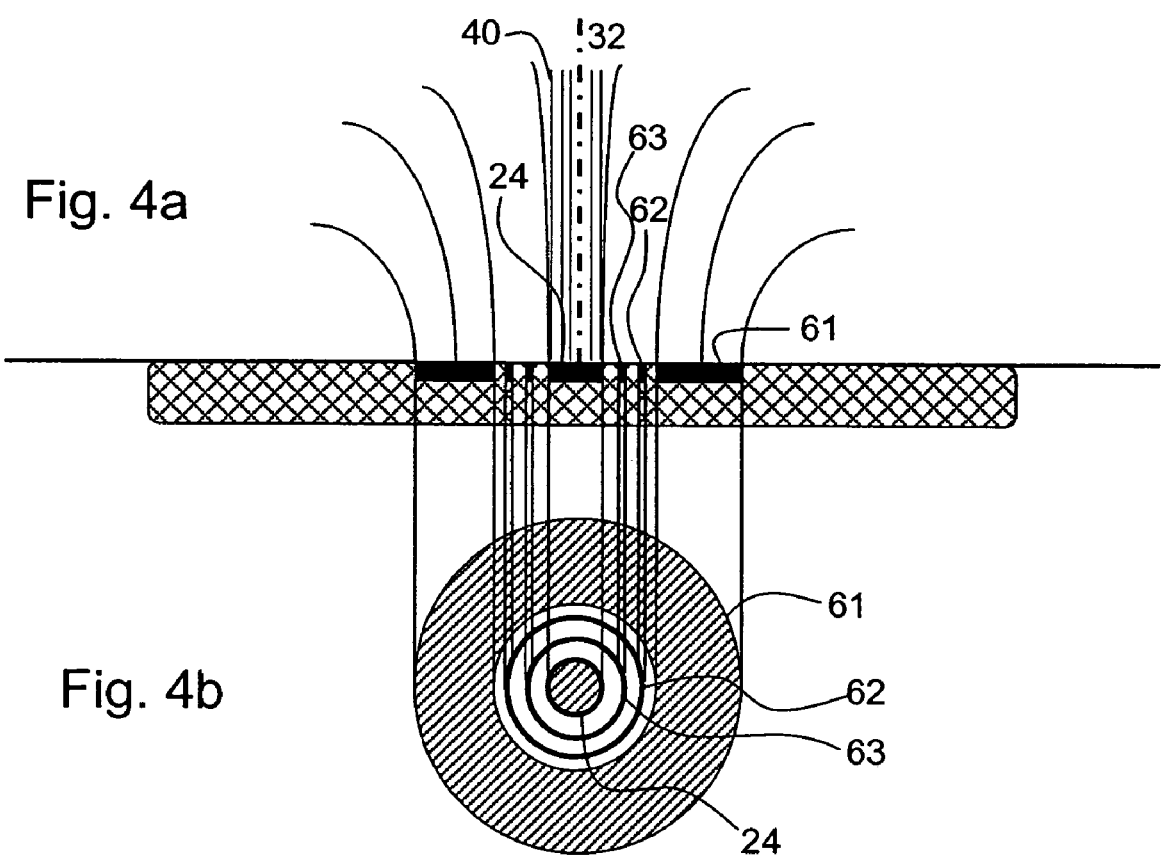
FIGS. 4a–b are schematic illustration of a side view (FIG. 4a) and a top view (FIG. 4b) of the apparatus for measuring electrical resistance in an embodiment in which the active contouring device comprises electrodes having circular-like shapes, according to a preferred embodiment of the present invention.

In another embodiment, contouring device 30 is an active contouring device. FIG. 3 and FIGS. 4a–b are schematic illustrations of apparatus 20 when device 30 is an active contouring device. In this embodiment, contouring device 30 preferably comprises an arrangement of additional electrodes 38. Electrodes 38 serve for generating an additional electric filed, which, together with the electric field generated by electrodes 24 results in an effective electric field 40, contoured along contour 32.

Any number and shape of additional electrodes can be used, provided the resultant effective electric field is contoured along contour 32.

For example, referring to FIG. 3, device 30 may comprise three pairs of linear additional electrodes, 41a–41b, 42a–42b and 43a–43b, respectively connected to leads 51, 52 and 53 of voltage source 28 (not shown, see FIG. 2). According to the presently preferred embodiment of the invention the voltage across electrode pair 41 is selected such that the potential difference between electrodes 42a and 43a and the potential difference between electrodes 42b and 43b is substantially zero. One of ordinary skill in the art will appreciate that with such configuration, effective electric field 40 is substantially uniform near electrode 24 and non-uniform in other regions. Thus, electrode pairs 41, 42 and 43 contour the electric field along contour 32 as desired.

Reference is now made to FIGS. 4a–b which are simplified illustration of a side view (FIG. 4a) and a top view (FIG. 4b) of apparatus 20 in an embodiment in which device 30 comprises three additional electrodes, designated 61, 62 and 63 each having a circular-like (e.g., circular, elliptical etc.) shape. Similarly to the embodiment shown in FIG. 3, the voltage across electrode 61 is preferably selected such that the potential difference between electrodes 62 and 63 is substantially zero, thereby ensuring that effective electric field 40 is substantially uniform near electrode 24 hence being contoured along contour 32.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which, together with the above descriptions, illustrates the invention in a non limiting fashion.

Measurements of electrical resistivity were performed on different samples of cement, according to a preferred embodiment of the present invention. The following measurements were continuously taken when the age of the mix was below 48 hours.

Figure 5:
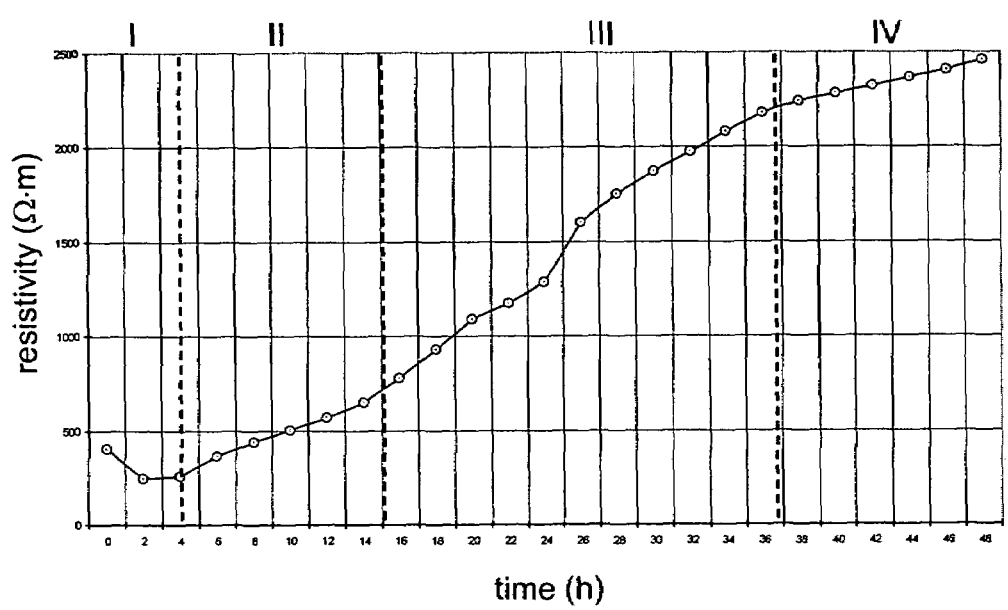
FIG. 5 shows the electrical resistivity in units of $\Omega \cdot m$, as a function of time in hours, as measured for a standard cement-sand mix, according to a preferred embodiment of the present invention.

FIG. 5 shows the electrical resistivity, $\rho$, in units of $\Omega\cdot m$, as a function of time, $\tau$, in hours, as measured for a standard cement-sand mix (according to the EU standard EN-196, Part 1: Methods of testing cement; Determination of strength"). The mix was prepared using CEM-1 Type cement, strength class 42.5 N (EU standard EN-197, Part 1: "Composition, specification and conformity criteria for common cements"). As demonstrated in FIG. 5, the four aforementioned structural states of the mix, designated on FIG. 5 by roman numerals I–IV, can be identified by inspecting the resistivity time-dependence, $\rho(\tau)$. Specifically, transitions between states were observed in the following values of $\tau$: 4 (transition from state I to state II), 15 (transition from state II to state III) and 37 (transition from state III to state IV). An additional functional transition in which the increment of resistivity is being moderated, was observed at the time interval between about 20 hours and about 25 hours. This transition characterizes the formation of three-dimensional cells, prior to the building up of a continuous crystalline frame, in which the electrical resistivity is stabilized, as further detailed hereinabove.

Figure 6:
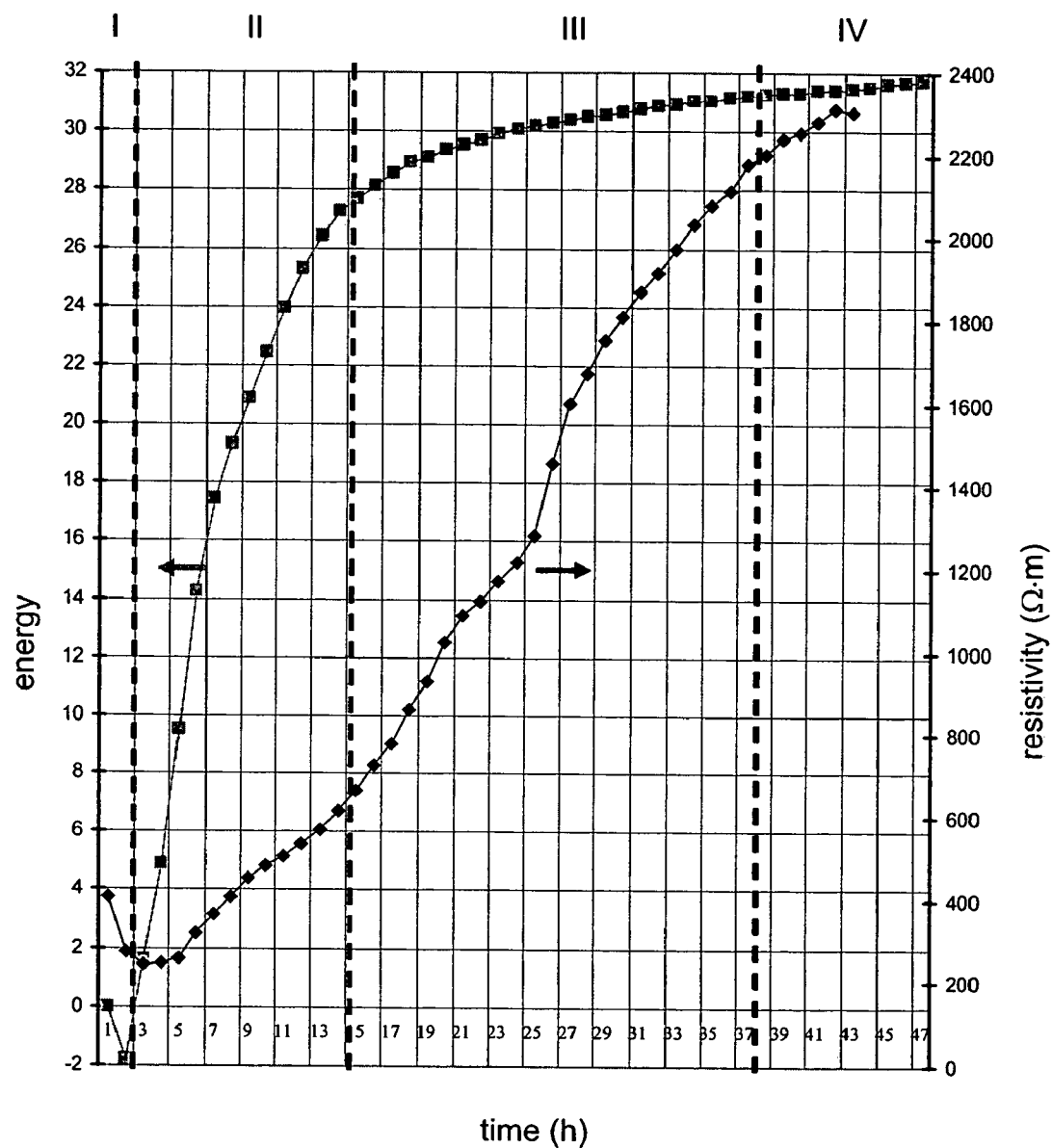
FIG. 6 shows a comparison between the energy of bound water, in units of J/s, and the electrical resistivity in units of $\Omega \cdot m$, for the standard cement-sand mix, according to a preferred embodiment of the present invention.

FIG. 6 shows a comparison between the energy of the bound water, in units of J/s, and the electrical resistivity, for standard cement-sand mix. As shown, the electrical resistivity is more sensitive to transitions between the structural changes in the mix.

Figure 7:
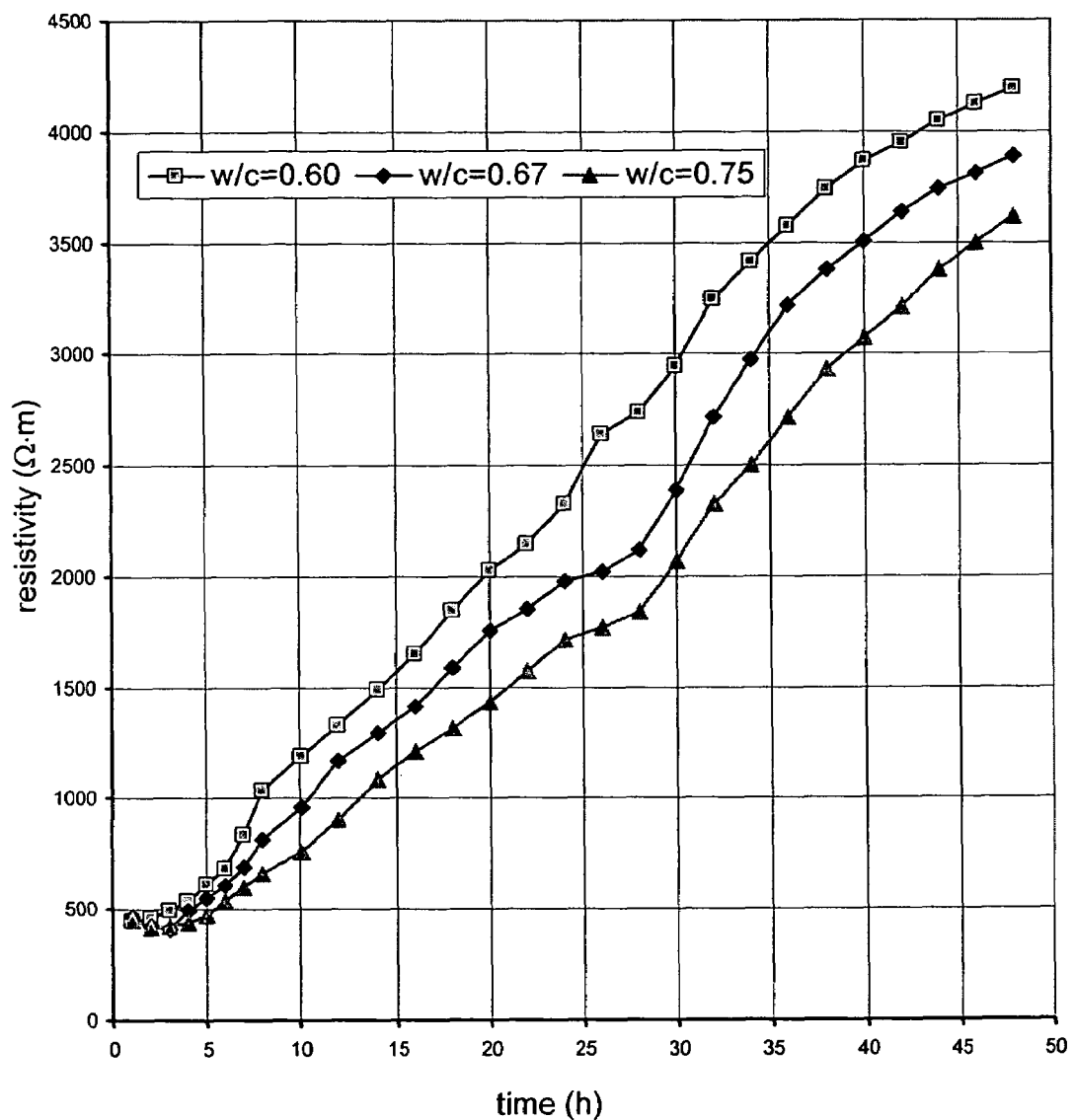
FIG. 7 shows the time-dependence of the electrical resistivity in units of $\Omega \cdot m$, of a fine-grained concrete mix, using fine-grained dolomite aggregates purchased from Kohav-Ha-Shahar quarry, Israel.
Figure 8:
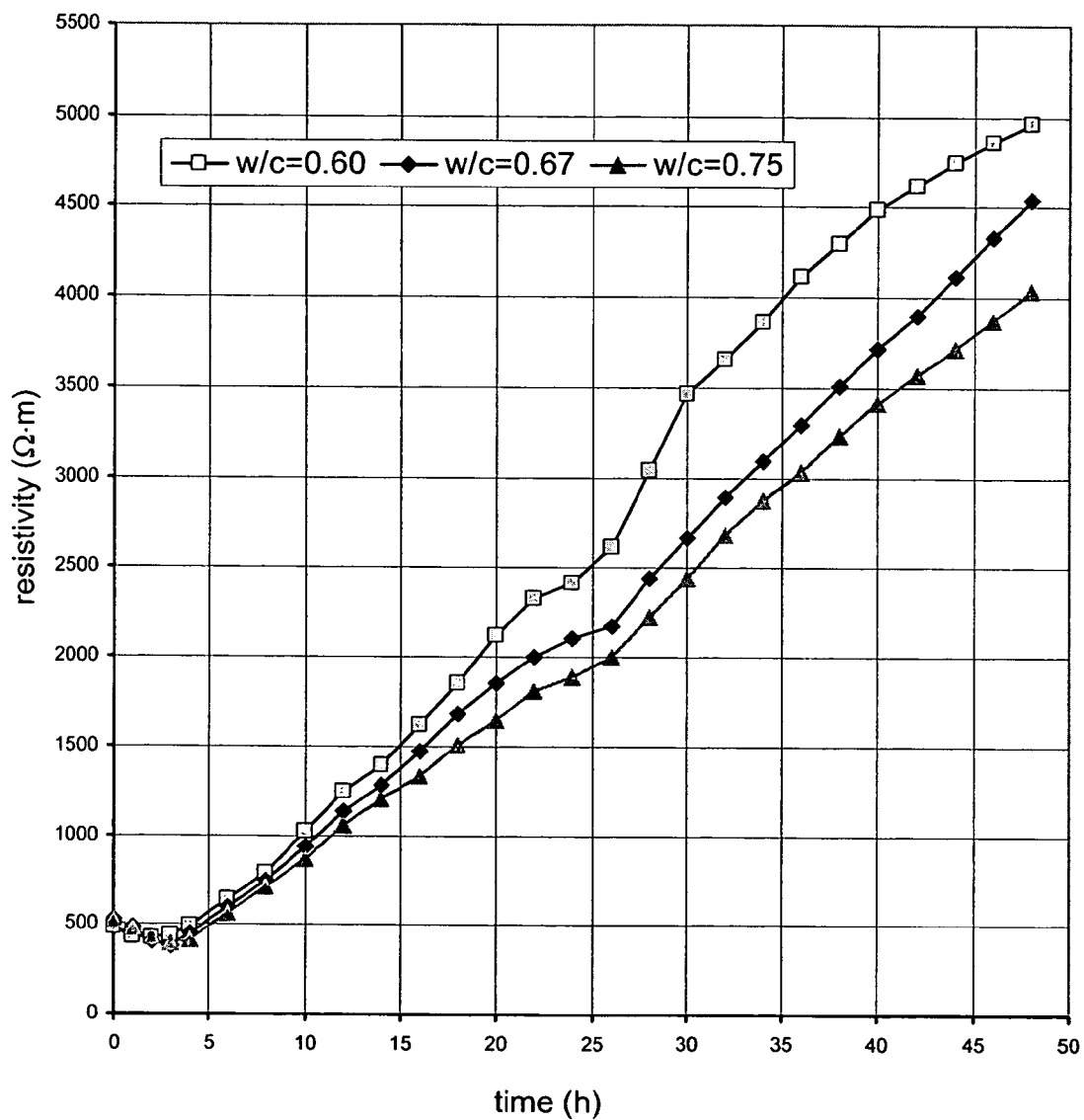
FIG. 8 shows the time-dependence of the electrical resistivity in units of $\Omega \cdot m$, of a fine-grained concrete mix, using fine-grained dolomite aggregates purchased from Shfaram quarry, Israel.

FIG. 7 and FIG. 8 show the time-dependence of the electrical resistivity, $\rho(\tau)$, in units of $\Omega\cdot m$, of fine-grained concrete mixes, for water/cement ratios of 0.60, 0.67 and 0.75. The mixes were prepared using fine-grained dolomite aggregates purchased from Kohav-Ha-Shahar quarry, Israel (FIG. 7) and Shfaram quarry, Israel (FIG. 8), with a cement:send:aggregates composition of 1:2:3.

As shown in FIGS. 7–8, similar functional transitions were observed during the first 48 hours of hardening, irrespectively of the water/cement ratio or the type of aggregates. The functional transitions shown in FIGS. 7–8 are in agreement with the functional transitions of the standard cement-sand mix of FIG. 5 and FIG. 6. In addition, the fine-grained concrete mixes exhibits the aforementioned increment moderation of $\rho(\tau)$, which characterizes the formation of three-dimensional cells in the third structural state of the mix. Similarly to the cement-sand mix, the moderation was observed approximately between $\tau=20$ hours and $\tau=25$ hours.

Figure 9A:
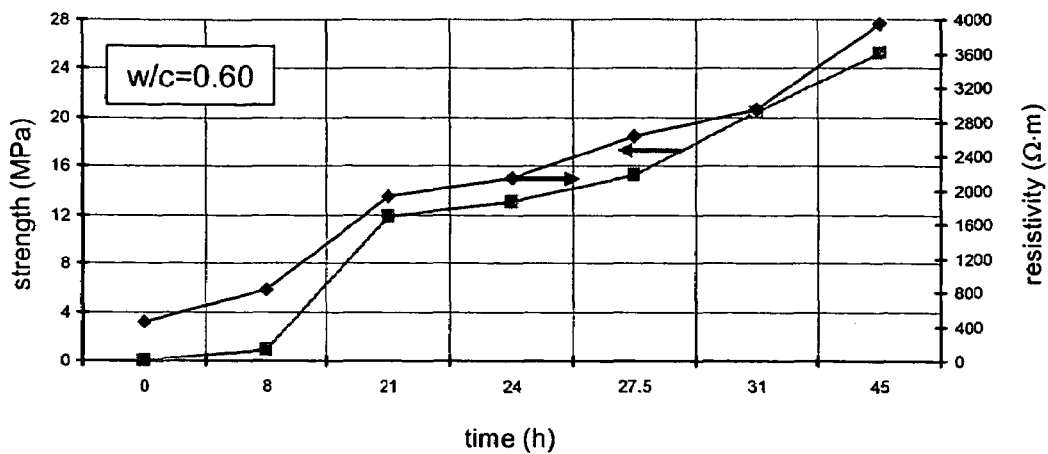
FIGS. 9a–c show comparisons between the time-dependences of the compressive strength in units of MPa, and the electrical resistivity in units of $\Omega \cdot m$, of the fine-grained concrete mixes of FIG. 7, for water cement ratios of 0.60 (FIG. 9a), 0.67 (FIG. 9b) and 0.75 (FIG. 9c)
Figure 9B:
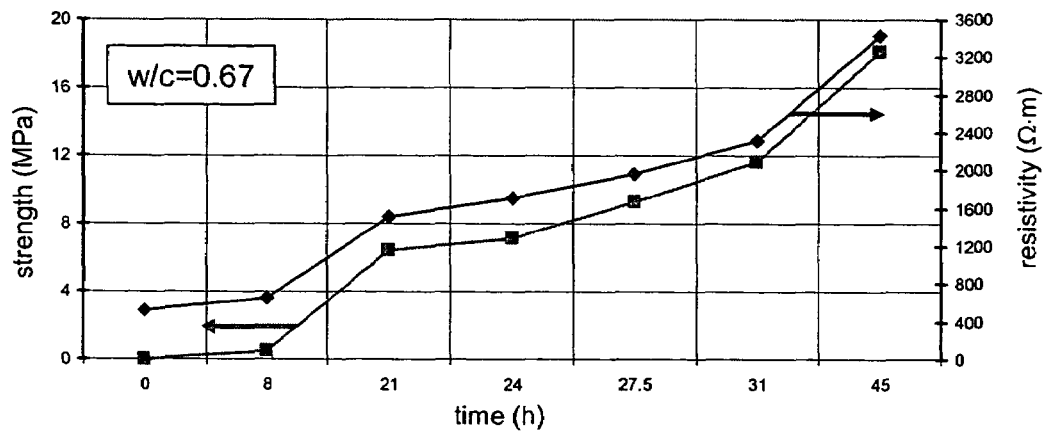
Figure 9C:
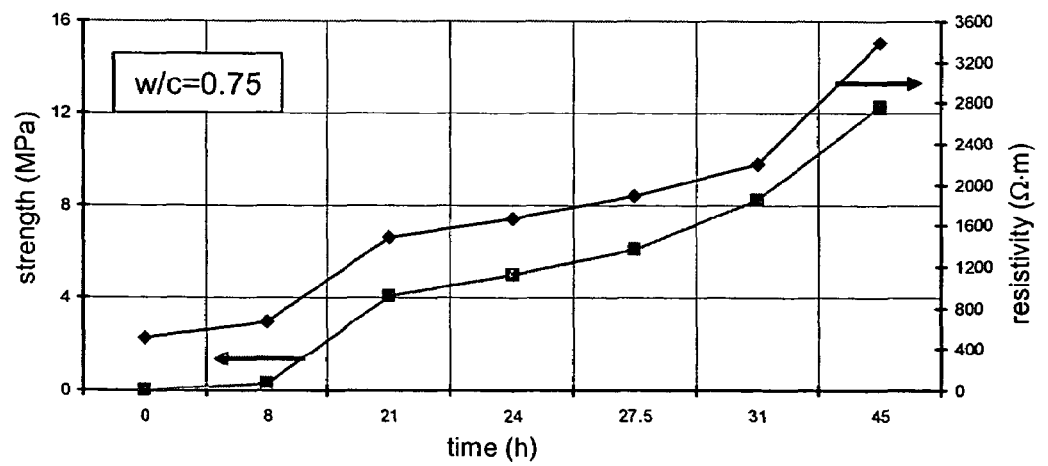
Figure 10A:
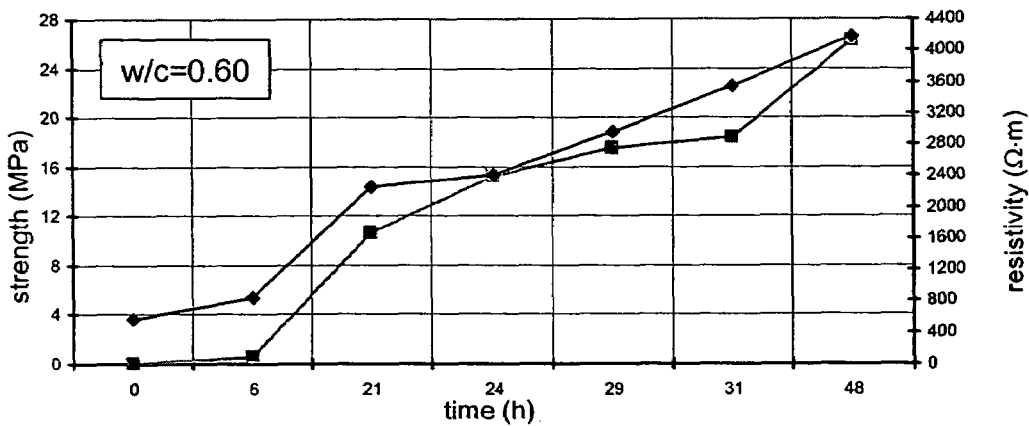
FIGS. 10a–c show comparisons between the time-dependences of the compressive strength in units of MPa, and the electrical resistivity in units of $\Omega \cdot m$, of the fine-grained concrete mixes of FIG. 8, for water cement ratios of 0.60 (FIG. 10a), 0.67 (FIG. 10b) and 0.75 (FIG. 10c)
Figure 10B:
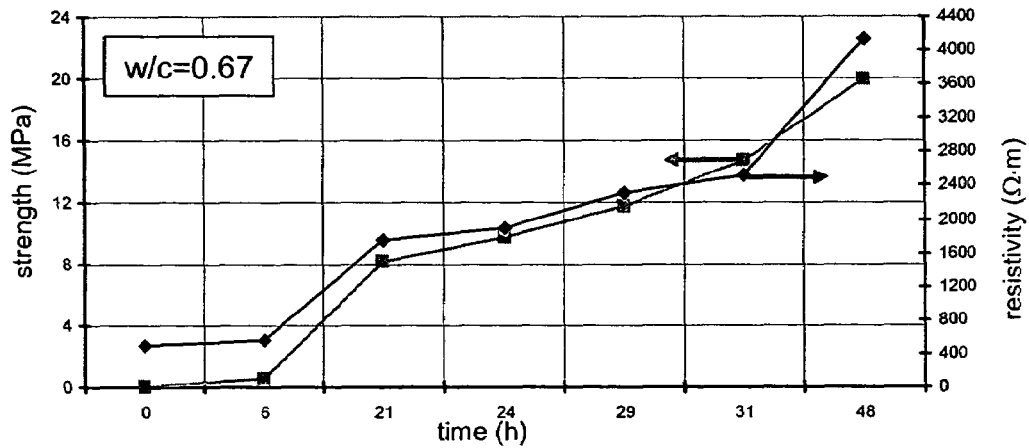
Figure 10C:
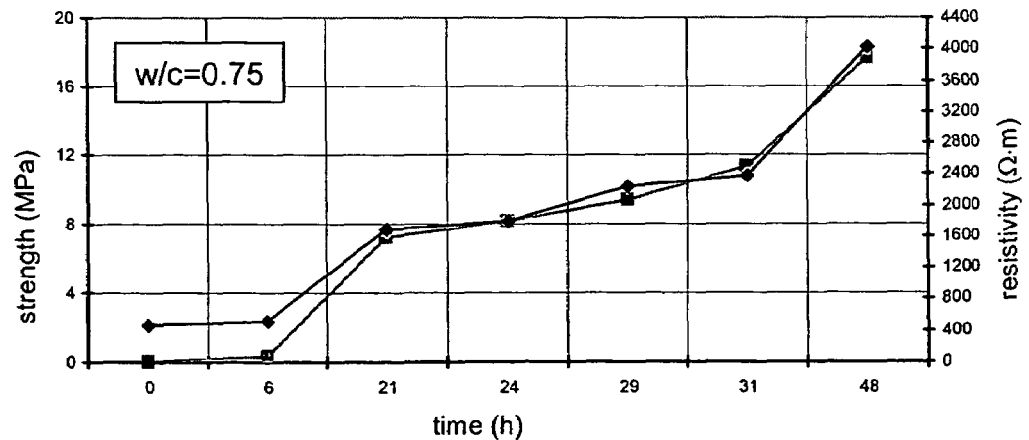

FIGS. 9a–c and FIGS. 10a–c show comparisons between the time-dependences of the compressive strength, $R(\tau)$, in units of MPa, and the electrical resistivity, $\rho(\tau)$, in units of $\Omega\cdot m$, of the fine-grained concrete mixes of FIGS. 7 and 8, respectively. Shown are water/cement ratios of 0.60 (FIGS. 9a and 10a), 0.67 (FIGS. 9b and 10b) and 0.75 (FIGS. 9c and 10c). As shown in FIGS. 9a–10c, the curves $R(\tau)$ and $\rho(\tau)$ exhibit similar behavior, in particular the increment moderation, observed approximately between $\tau=20$ hours and $\tau=25$ hours. Thus, in accordance with preferred embodiments of the present invention, functional transitions of $\rho(\tau)$ can be used for determining the strengthening state of the material.

Figure 11:
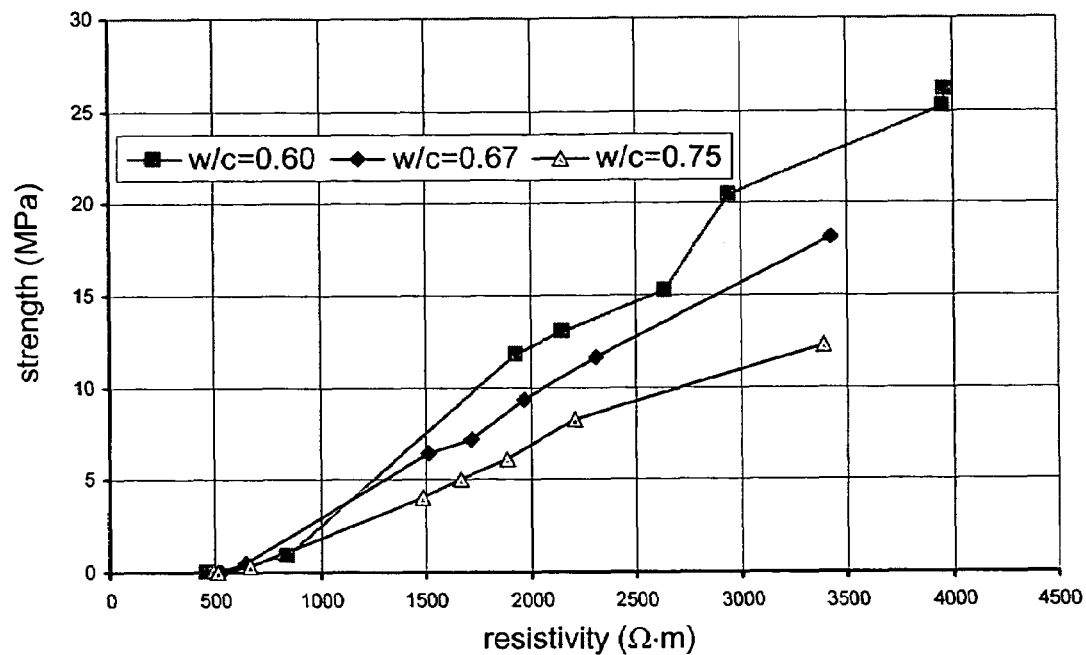
FIG. 11 show graphical representation of a correlation function, which correlate between the time-dependences of the electrical resistance and the compressive strength for the fine-grained concrete mixes of FIG. 7.
Figure 12:
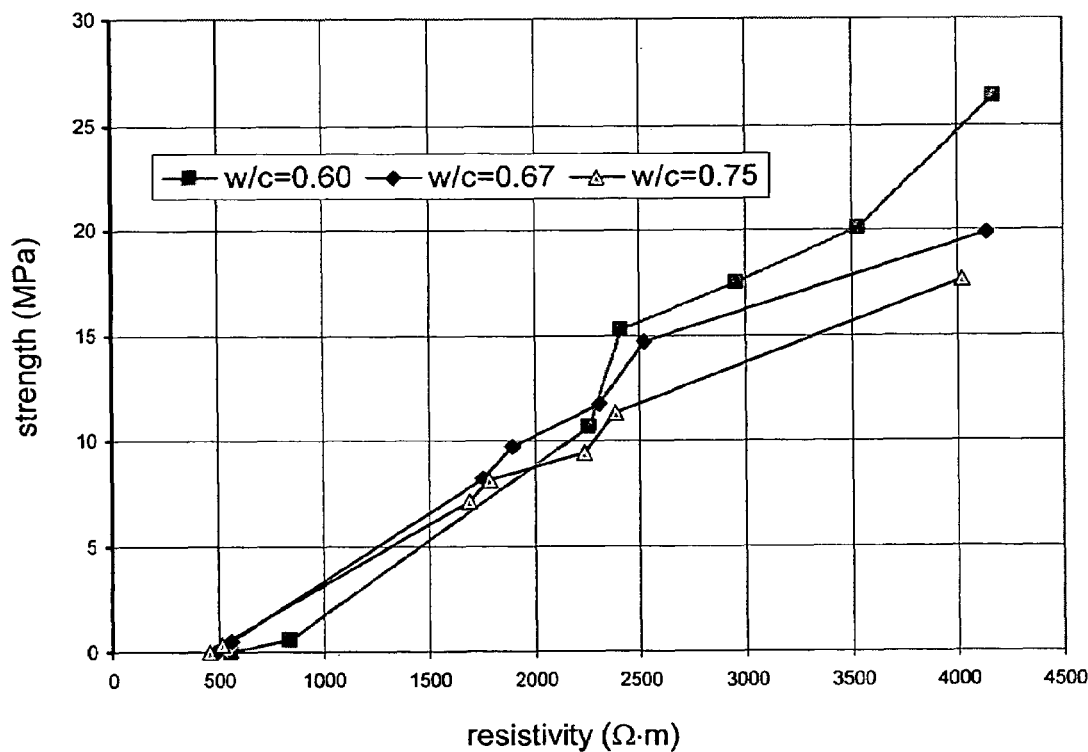
FIG. 12 show graphical representation of a correlation function, which correlate between the time-dependences of the electrical resistance and the compressive strength for the fine-grained concrete mixes of FIG. 8.

FIG. 11 and FIG. 12 show graphical representation of the correlation function, $\psi$, as determined by correlating between the time-dependences of the electrical resistance, $\rho$, and the compressive strength, R, for the fine-grained concrete mixes of FIGS. 7 and 8, respectively. $\psi(\rho)$ can thus be used for determining the compressive strength, for different values of the electrical resistivity. For example, $\psi(\rho)$ can be used for determining the compressive strength at, say, $\tau=50$ hours, from which the compressive strength is known to have a logarithmic dependence.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of monitoring a strengthening process of a chemically active material having a liquid phase and a non-liquid phase, the method comprising:
   (a) continuously measuring at least one physical parameter characterizing the liquid phase;

(b) extracting a time-dependence of said at least one physical parameter, so as to identify functional transitions in said time-dependence; and (c) using said functional transitions to determine a strengthening state of the chemically active material;

thereby monitoring the strengthening process of the chemically active material.

2. The method of claim 1, wherein said at least one physical parameter is selected from the group consisting of electrical resistivity and electrical resistance.

3. The method of claim 2, wherein said step of continuous measurement comprises positioning the chemically active material in a container and generating an electric field within the chemically active material, so as to measure said resistivty or resistance of the chemically active material.

4. The method of claim 3, wherein said generation of said electric field is by at least two electrodes and further wherein said continuous measurement comprises measuring at least one component of electrical current flowing through said at last two electrodes.

5. The method of claim 4, wherein said at least one component of electrical current is a real-part of said electrical current.

6. The method of claim 4, wherein said at least one component of electrical current is an imaginary-part of said electrical current.

7. The method of claim 3, further comprising contouring said electric field substantially along a predetermined contour within said chemically active material.

8. The method of claim 7, wherein said contouring said electric field is by positioning a dielectric partition in a manner such that electric field lines of said electric field bypass said dielectric partition hence being contoured along said predetermined contour.

9. The method of claim 7, wherein said contouring said electric field is by generating an additional electric field in a manner such that an effective electric field, defined by a superposition of said electric field and said additional electric field, is contoured along said predetermined contour.

10. The method of claim 1, wherein said functional transitions are characterized by a sign inversion of an nth derivative of said time-dependence, said n being a positive integer.

11. The method of claim 1, wherein said functional transitions comprise deviations of said time-dependence from smoothness.

12. The method of claim 1, wherein said functional transitions comprise at least one inflection point of said time-dependence.

13. The method of claim 1, wherein said step of continuous measurement is executed substantially in a constant volume.

14. The method of claim 1, wherein said step of continuous measurement is initiated sufficiently before a compressive strength of the chemically active material develops a logarithmic time-dependence.

15. The method of claim 14, wherein said step of continuous measurement is initiated when an age of the chemically active material is below about 150 hours.

16. The method of claim 14, wherein said step of continuous measurement is initiated when an age of the chemically active material is below about 100 hours.

17. The method of claim 14, wherein said step of continuous measurement is initiated when an age of the chemically active material is below about 50 hours.

18. The method of claim 14, further comprising correlating between said time-dependence of said at least one physical parameter and said compressive strength, thereby obtaining a correlation function.

19. The method of claim 18, further comprising using said correlation function for parameterizing said logarithmic time-dependence of said compressive strength curve.

20. An apparatus for measuring an electrical resistance of a chemically active material, the apparatus comprising:

(a) a container for holding the chemically active material;

(b) at least two electrodes for generating an electric field within the chemically active material and sensing a resistance of the chemically active material to said electric field; and (c) a contouring device for contouring said electric field substantially along a predetermined contour within said chemically active material, said contouring device comprising a passive contouring device having a dielectric partition, positioned between a first electrode and a second electrode of said least two electrodes, wherein a size and shape of said dielectric partition is selected such that electric field lines of said electric field bypass said dielectric partition hence being contoured along said predetermined contour.

21. The apparatus of claim 20, wherein said contouring device comprises an active contouring device.

22. The apparatus of claim 21, wherein said active contouring device comprises an arrangement of additional electrodes designed and configured such that an effective electric field, defined by a superposition of an electric field generated by said additional electrodes and said electric field generated by said at least two electrodes, is contoured along said predetermined contour.

23. The apparatus of claim 21, wherein said arrangement of additional electrodes comprises at least one linear electrode.

24. The apparatus of claim 21, wherein said arrangement of additional electrodes comprises at least one electrode having a circular-like shape.

25. The apparatus of claim 24, wherein said arrangement of additional electrodes comprises a first electrode, a second electrode and a third electrode, and further wherein a potential difference across said first electrode is selected such that a potential difference between said second electrode and said third electrode is substantially zero at all times.

26. The apparatus of claim 21, wherein said arrangement of additional electrodes comprises a first pair of electrodes, a second pair of electrodes and a third pair of electrodes, and further wherein a potential difference across said first pair of electrodes is selected such that a potential difference between said second pair of electrodes and said third pair of electrodes is substantially zero at all times.

27. A method of determining a strengthening state of a chemically active material from a series of measurements of at least one physical parameter characterizing a liquid phase of the chemically active material, the method comprising extracting a time-dependence of said at least one physical parameter, so as to identify functional transitions in said time-dependence, and using said functional transitions to determine the strengthening state of the chemically active material.

28. The method of claim 27, wherein said at least one physical parameter is selected from the group consisting of electrical resistivity and electrical resistance.

29. The method of claim 27, wherein said functional transitions are characterized by a sign inversion of an nth derivative of said time-dependence, said n being a positive integer.

30. The method of claim 27, wherein said functional transitions comprise deviations of said time-dependence from smoothness.

31. The method of claim 27, wherein said functional transitions comprise at least one inflection point of said time-dependence.

32. The method of claim 27, being executed when an age of the chemically active material is below about 150 hours.

33. The method of claim 27, being executed when an age of the chemically active material is below about 100 hours.

34. The method of claim 27, being executed when an age of the chemically active material is below about 50 hours.

35. The method of claim 27, further comprising correlating between said time-dependence of said at least one physical parameter and a compressive strength of the chemically active material, thereby obtaining a correlation function.

36. The method of claim 35, further comprising using said correlation function for parameterizing a curve of said compressive strength, said curve having a logarithmic shape.

37. An apparatus for determining a strengthening state of a chemically active material from a series of measurements of at least one physical parameter characterizing a liquid phase of the chemically active material, the apparatus comprising:
   (a) an inputting unit for inputting the series of measurements;
   (b) an extractor for extracting a time-dependence of said at least one physical parameter; and
   (c) an identifier for identifying functional transitions in said time-dependence, and using said functional transitions for determining the strengthening state of the chemically active material.

38. The apparatus of claim 37, wherein said at least one physical parameter is selected from the group consisting of electrical resistivity and electrical resistance.

39. The apparatus of claim 37, wherein said functional transitions are characterized by a sign inversion of an nth derivative of said time-dependence, said n being a positive integer.

40. The apparatus of claim 37, wherein said functional transitions comprise deviations of said time-dependence from smoothness.

41. The apparatus of claim 37, wherein said functional transitions comprise at least one inflection point of said time-dependence.

42. The apparatus of claim 37, further comprising a correlator for correlating between said time-dependence of said at least one physical parameter and a compressive strength of the chemically active material, thereby obtaining a correlation function.

43. The apparatus of claim 42, further comprising a parameterizer for parameterizing a curve of said compressive strength, using said correlation function, wherein said curve has a logarithmic shape.

44. A system for monitoring a strengthening process of a chemically active material having a liquid phase and a non-liquid phase, the system comprising:
   (a) a measuring apparatus for continuously measuring at least one physical parameter characterizing the liquid phase; and
   (b) an analyzing apparatus, for determining a strengthening state of the chemically active material thereby monitoring the strengthening process, the analyzing apparatus comprises an extractor, for extracting a time-dependence of said at least one physical parameter, and an identifier, for identifying functional transitions in said time-dependence and using said functional transitions for determining said strengthening state.

45. The system of claim 44, wherein said at least one physical parameter is selected from the group consisting of electrical resistivity and electrical resistance.

46. The system of claim 45, wherein said measuring apparatus comprises:
   (i) a container for holding the chemically active material;
   (ii) at least two electrodes for generating an electric field within the chemically active material and sensing a resistance of the chemically active material to said electric field; and
   (iii) a contouring device for contouring said electric field substantially along a predetermined contour within said chemically active material.

47. The system of claim 46, wherein said contouring device comprises a passive contouring device.

48. The system of claim 46, wherein said passive contouring device comprises a dielectric partition, positioned between a first electrode and a second electrode of said least two electrodes, and further wherein a size and shape of said dielectric partition is selected such that electric field lines of said electric field bypass said dielectric partition hence being contoured along said predetermined contour.

49. The system of claim 46, wherein said contouring device comprises an active contouring device.

50. The system of claim 49, wherein said active contouring device comprises an arrangement of additional electrodes designed and configured such that an effective electric field, defined by a superposition of an electric field generated by said additional electrodes and said electric field generated by said at least two electrodes, is contoured along said predetermined contour.

51. The system of claim 49, wherein said arrangement of additional electrodes comprises at least one linear electrode.

52. The system of claim 49, wherein said arrangement of additional electrodes comprises at least one electrode having a circular-like shape.

53. The system of claim 49, wherein said arrangement of additional electrodes comprises a first electrode, a second electrode and a third electrode, and further wherein a potential difference across said first electrode is selected such that a potential difference between said second electrode and said third electrode is substantially zero at all times.

54. The system of claim 49, wherein said arrangement of additional electrodes comprises a first pair of electrodes, a second pair of electrodes and a third pair of electrodes, and further wherein a potential difference across said first pair of electrodes is selected such that a potential difference between said second pair of electrodes and said third pair of electrodes is substantially zero at all times.

55. The system of claim 44, wherein said functional transitions are characterized by a sign inversion of an nth derivative of said time-dependence, said n being a positive integer.

56. The system of claim 44, wherein said functional transitions comprise deviations of said time-dependence from smoothness.

57. The system of claim 44, wherein said functional transitions comprise at least one inflection point of said time-dependence.

58. The system of claim 44, further comprising a correlator for correlating between said time-dependence of said at least one physical parameter and a compressive strength of the chemically active material, thereby obtaining a correlation function.

59. The system of claim 58, further comprising a parameterizer for parameterizing a curve of said compressive strength, using said correlation function, wherein said curve has a logarithmic shape.

* * * * *